United States Patent
Mack et al.

(10) Patent No.: US 11,458,145 B2
(45) Date of Patent: *Oct. 4, 2022

(54) METHODS OF ADMINISTERING INTRAVENOUS MELOXICAM IN A BOLUS DOSE

(71) Applicant: BAUDAX BIO, INC., Malvern, PA (US)

(72) Inventors: Randall J. Mack, Malvern, PA (US); Alex Freyer, Malvern, PA (US)

(73) Assignee: BAUDAX BIO, INC., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/297,095

(22) Filed: Mar. 8, 2019

(65) Prior Publication Data

US 2019/0275054 A1 Sep. 12, 2019
US 2021/0100811 A9 Apr. 8, 2021

Related U.S. Application Data

(63) Continuation-in-part of application No. 16/297,020, filed on Mar. 8, 2019, now Pat. No. 10,881,663.

(60) Provisional application No. 62/749,407, filed on Oct. 23, 2018, provisional application No. 62/652,656, filed on Apr. 4, 2018, provisional application No. 62/640,232, filed on Mar. 8, 2018.

(51) Int. Cl.

| | |
|---|---|
| *A61K 31/4709* | (2006.01) |
| *A61K 9/06* | (2006.01) |
| *A61K 47/10* | (2017.01) |
| *A61K 47/12* | (2006.01) |
| *A61P 17/10* | (2006.01) |
| *A61P 17/00* | (2006.01) |
| *A61P 17/04* | (2006.01) |
| *A61P 31/04* | (2006.01) |
| *A61K 31/5415* | (2006.01) |
| *A61K 9/10* | (2006.01) |
| *A61K 9/00* | (2006.01) |
| *A61P 29/00* | (2006.01) |
| *A61K 47/28* | (2006.01) |
| *A61K 47/32* | (2006.01) |
| *A61P 25/00* | (2006.01) |

(52) U.S. Cl.
CPC ........ *A61K 31/5415* (2013.01); *A61K 9/0019* (2013.01); *A61K 9/10* (2013.01); *A61K 47/28* (2013.01); *A61K 47/32* (2013.01); *A61P 29/00* (2018.01); *A61P 25/00* (2018.01)

(58) Field of Classification Search
CPC .... A61K 31/5415; A61K 9/0019; A61P 29/00
See application file for complete search history.

(56) References Cited

U.S. PATENT DOCUMENTS

| | | | |
|---|---|---|---|
| 10,463,673 B2 | 11/2019 | Cooper et al. | |
| 2004/0229038 A1* | 11/2004 | Cooper | A61K 9/145 428/402.21 |
| 2005/0288280 A1* | 12/2005 | Friton | A61K 31/5415 514/226.5 |
| 2009/0004262 A1 | 1/2009 | Shaw et al. | |
| 2010/0316725 A1 | 12/2010 | Ryde et al. | |
| 2017/0157061 A1* | 6/2017 | Cooper | A61K 9/0053 |
| 2019/0275053 A1 | 9/2019 | Mack et al. | |

FOREIGN PATENT DOCUMENTS

| | | |
|---|---|---|
| EP | 3090731 B1 | 11/2016 |
| EP | 3777862 A1 | 2/2021 |
| WO | 2020086737 A1 | 4/2020 |
| WO | 2020097338 A1 | 5/2020 |

OTHER PUBLICATIONS

Walliser et al. BMC Veterinary Research (2015), 11(13), p. 2-8.*
Recro Pharma Initiates Pivotal-Phase III Clinical of abdominoplasty surgery_Jan. 27, 2016.*
FDA formula N1539_Jul. 26, 2017.*
Recro Pharma Presents Clinical Data at PAINWeek 2016—MarketWatch, published Sep. 7, 2016.*
International Search Report and Written Opinion dated May 24, 2019 for International Application No. PCT/US2019/21354, 9 pages.
Gan, T. J. et al., "The Shortened Infusion Time of Intravenous Ibuprofen, Part 2: A Multicenter, Open-label, Surgical Surveillance Trial to Evaluate Safety," Clinical Therapeutics, 37(2):368-375 (2015).
Gottlieb, I. J. et al., "Evaluation of the safety and efficacy of an intravenous nanocrystal formulation of meloxicam in the management of moderate-to-severe pain after bunionectomy," Journal of Pain Research, 11:383-393 (2018).
International Search Report and Written Opinion dated Jan. 10, 2020 for International Application No. PCT/US2019/060278.
Aschoff, "Expecting Additional Phase 3 Validation for Meloxicam IV by YE16—Manufacturing Business Provides Valuation Floor: Initiating BUY/$22 TP," Opus National Capital Markets: Biotechnology; Nov. 9, 2016, pp. 1-15.
Boulton-Jones et al., "Meloxicam Pharmacokinetics in Renal Impairment," Black Science Ltd; Br J Clin Pharmacol 1997; 43: pp. 35-40.
European Search Report for European Patent Application No. 19764737.3 dated Nov. 11, 2021.
Pollak et al., "Efficacy and Safety of Intravenous Meloxicam in Patients with Moderate-to-Severe Pain Following Bunionectomy: A Randomized, Double-Blind, Placebo-Controlled Trial," Clinical Journal of PAIN, Oct. 1, 2018, vol. 34, No. 10, pp. 918-926.
Berkowitz et al. (Abstract) "Safety and Opioid Use Following Major Orthopedic Surgery in a Phase 3, Placebo-Controlled Study of Intravenous Meloxicam" 2017, Postgraduate Medicine 129 SUPPL1: 56-57, Abstract No. 77.

(Continued)

*Primary Examiner* — Layla Soroush
(74) *Attorney, Agent, or Firm* — DLA Piper LLP (US)

(57) ABSTRACT

The present disclosure relates to meloxicam bolus formulations and methods of administering the same intravenously, for treatment of pain, which can provide fast onset of pain relief suitable for management of acute moderate to severe pain.

13 Claims, 3 Drawing Sheets

(56) References Cited

OTHER PUBLICATIONS

Bergese et al. (Abstract) "Safety and Opioid Use in a Phase 3, Placebo-Controlled Study of Intravenous Meloxicam Following Major Surgery" Postgraduate Medicine 2017, 129 SUPPL1: 57-58, Abstract No. 78.
Melson et al. (Abstract) "Safety and Opioid Use in Subjects of Advanced Age with Impaired Renal Function in a Phase 3, Placebo-Controlled Study of Intravenous Meloxicam Following Major Surgery" Postgraduate Medicine 2017, vol. 129 No. SUPPL 1, pp. 58-59, Abstract No. 79.
Schmid et al., "Pharmacokinetics and Metabolic Pattern after Intravenous Infusion and Oral Administration to Healthy Subjects," pp. 1206-1213 (1995).
Jan. 2016 Recro Pharma Exhibit 99.1.†
Recro Pharma Presents Clinical Data at PAINWeek 2016—MarketWatch Published: Sep. 7, 2016 4:05 p.m. ET.†

\* cited by examiner
† cited by third party

METHODS OF ADMINISTERING INTRAVENOUS MELOXICAM IN A BOLUS DOSE

CROSS REFERENCE TO RELATED APPLICATIONS

This application claims the benefit under 35 U.S.C. § 119(e) of U.S. Provisional Patent Application No. 62/640,232, filed Mar. 8, 2018; U.S. Provisional Patent Application No. 62/652,656, filed Apr. 4, 2018; and U.S. Provisional Patent Application No. 62/749,407, filed Oct. 23, 2018. The contents of these applications are incorporated herein by reference in their entireties for all purposes.

FIELD OF THE DISCLOSURE

The present disclosure relates to methods of administering meloxicam for treatment of pain, including intravenous bolus administration.

BACKGROUND OF THE DISCLOSURE

Meloxicam (4-hydroxy-2-methyl-N-(5-methyl-2-thiazolyl)-2H-1,2-benzothiazine-3-carboxamide-1,1-dioxide) is a long-acting non-steroidal-anti-inflammatory drug (NSAID) that possesses anti-inflammatory, analgesic, and antipyretic activities, which are believed to be related to the inhibition of cyclooxygenase (COX) and subsequent reduction in prostaglandin biosynthesis. Meloxicam has been marketed by Boehringer Ingelheim Pharmaceuticals, Inc. since the 1990's as an oral agent, Mobic®. Mobic is used for treatment of symptoms of osteoarthritis and rheumatoid arthritis.

Oral meloxicam, however, has a slow onset of action, largely due to poor water solubility. The oral form has a prolonged absorption time, with the time of maximum observed plasma concentration ($t_{max}$) being approximately 5-7 hours following oral administration, which is consistent with its poor water solubility. Because of the slow onset of action, oral meloxicam is not used for the treatment of acute pain.

Intravenous (IV) administration of the NSAID ibuprofen was approved in 2009 for pain management; however, an infusion time of 30 minutes is required and it must be administered every 6 hours. See CALDOLOR® Prescribing Information. Further, patients receiving IV administration of NSAIDs report relatively high rates of injection site pain or discomfort (e.g., 16%-24% reported), which prohibits faster administration times. See Bergese, S. G., et al., *Clinical Therapeutics*, 2015, 37, 368-375. Therefore, current approved IV NSAID formulations have significant drawbacks Thus, there is a need for a method of administering meloxicam which can provide a faster onset of action, a longer therapeutic window, without the need for multiple injections a day. Such methods would be advantageous in providing rapid treatment for pain, including acute and mild to moderate or moderate to severe pain.

SUMMARY OF THE DISCLOSURE

In one embodiment of the disclosure, a method of treating pain in a patient in need thereof with meloxicam, comprising administering to the patient a bolus dose of meloxicam intravenously, wherein the meloxicam is at a concentration of about 30 mg/mL is disclosed.

In one embodiment of the method as disclosed herein, the meloxicam is in a form of meloxicam nanocrystals.

In one embodiment of the method as disclosed herein, the bolus dose of meloxicam is administered to the patient over the course of about 1 to about 60 seconds. In another embodiment, the bolus dose of meloxicam is administered to the patient over the course of about 5 to about 45 seconds. In other embodiments, the bolus dose of meloxicam is administered to the patient over the course of about 15 to about 30 seconds.

In one embodiment of the method as disclosed herein, the dose of meloxicam is in the range of from about 15 mg to about 180 mg. In some embodiments, the dose of meloxicam is about 30 mg. In another embodiment, the dose of meloxicam is about 60 mg.

In one embodiment of the method as disclosed herein, the dose of meloxicam is present in a volume of from about 0.5 mL to about 4 mL. In another embodiment, the dose of meloxicam is present in a volume of about 1 mL.

In one embodiment of the method as disclosed herein, the pain treated is post-surgical pain.

In one embodiment of the method as disclosed herein, the dose of meloxicam is administered after the patient has undergone a surgical procedure. In one embodiment, the surgical procedure is an open surgical procedure. In another embodiment, the surgical procedure is a laparoscopic surgical procedure. In other embodiments, the surgical procedure was performed on hard tissue. In some embodiments, the surgical procedure was performed on soft tissue.

In one embodiment of the method as disclosed herein, the pain treated is moderate to severe pain. In another embodiment, the pain treated is mild to moderate pain.

DETAILED DESCRIPTIONS OF THE DISCLOSURE

The present disclosure relates to methods of treating pain in a patient in need thereof with meloxicam. In one embodiment, the meloxicam is administered to a patient in a bolus dose. In another embodiment, the meloxicam is administered to a patient intravenously in a bolus dose. In some embodiments, the meloxicam is administered to a patient intravenously in a bolus dose at a concentration of about 30 mg/mL.

Definitions

It is to be understood that the terminology used herein is for the purpose of describing particular embodiments only and is not intended to be limiting.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

Following long-standing patent law convention, the terms "a", "an", and "the" refer to "one or more" when used in this application, including the claims. Thus, for example, reference to "a carrier" includes mixtures of one or more carriers, two or more carriers, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the present application. Generally the term "about", as used herein in references to a measurable value such as an amount of weight, time, dose, etc. is meant to encompass values within an acceptable degree of variability in the art. In some embodiments, degree of variability is based on FDA guidelines.

As used herein, "meloxicam" refers to 4-hydroxy-2-methyl-N-(5-methyl-2-thiazolyl)-2H-1,2-benzothiazine-3-carboxamide-1,1-dioxide, which has the structure as depicted below. The molecular weight is 351.4. Its molecular formula is $C_{14}H_{13}N_3O_4S_2$.

As used herein, the term "bolus dose" refers to a discrete amount of a medication or a drug, e.g., meloxicam, which is given within a specific time. The specific time over which the bolus dose is administered (also referred to herein as the infusion rate) may be any suitable time which provides rapid onset of action (i.e., pain relief) as measured by plasma $T_{max}$ of less than about 10 minutes and which does not cause significant injection site pain, such as a significant burning sensation. In some embodiments, the infusion time may be about 1 minute or less.

As used herein the term "$AUC_{inf}$" or "$AUC_{1-\infty}$" refers to area under the plasma concentration time curve from time zero to infinity or time zero to time of last quantifiable concentration.

Therapeutic Use

While oral administration of meloxicam is approved for treating inflammation (e.g., osteoarthritis and rheumatoid arthritis), currently available oral formulations of meloxicam are known to have a slow onset of action due to poor solubility of meloxicam. The slow onset of action of oral meloxicam has rendered meloxicam not appropriate for acute pain management (e.g., mild to moderate pain and/or moderate to severe pain).

The inventors discovered that an intravenous formulation of meloxicam may be administered in a bolus dose to provide a rapid onset of action of meloxicam that is critical for treatment of acute pain. Meloxicam nanocrystals significantly improves the solubility of the meloxicam, allowing for higher concentrations of meloxicam to be administered intravenously compared to an otherwise similar formulation in which meloxicam is not prepared as nanocrystals. Specifically, the inventors found that a bolus dose at a concentration of about 30 mg/mL was critical in achieving a rapid onset of action of meloxicam while being efficacious and safe for the treatment of acute pain (e.g., mild to moderate pain and/or moderate to severe pain). In contrast to other intravenous NSAIDs such as ibuprofen and acetaminophen, meloxicam nanocrystals surprisingly can be safely administered in a bolus dose without causing injection site pain. In addition, the inventors found that a bolus dose given over of about 60 seconds (e.g., about 1 to about 60 seconds, about 1 to 30 seconds, about 15 to about 30 seconds, etc.) was safe and effective for the treatment of pain for up to about 24 hours. The inventors also found that about 1 mL total volume for a bolus dose given over about 60 seconds (e.g., about 1 to about 60 seconds, about 1 to 30 seconds, about 15 to about 30 seconds, etc.) was safe and effective for the treatment of pain.

In some embodiments, the methods disclosed herein comprise administering to the patient a bolus dose of meloxicam intravenously, wherein the meloxicam is at a concentration of about 30 mg/mL.

In one embodiment, the meloxicam is in a form of meloxicam nanocrystals. In another embodiment, meloxicam nanocrystals are formed using Alkermes NanoCrystal™ technology. See U.S. Pat. No. 8,512,727 which is hereby incorporated by reference in its entirety for all purposes.

In one embodiment of the method as disclosed herein, the bolus dose of meloxicam is administered to the patient over the course of about 1 to about 60 seconds, including all values and subranges therebetween. That is, the bolus dose of meloxicam may be administered to patient in about 1 second, about 2 seconds, about 3 seconds, about 4 seconds, about 5 second, about 6 seconds, about 7 seconds, about 8 seconds, about 9 second, about 10 seconds, about 11 second, about 12 seconds, about 13 seconds, about 14 seconds, about 15 second, about 16 seconds, about 17 seconds, about 18 seconds, about 19 second, about 20 seconds, about 21 second, about 22 seconds, about 23 seconds, about 24 seconds, about 25 second, about 26 seconds, about 27 seconds, about 28 seconds, about 29 second, about 30 seconds, about 31 second, about 32 seconds, about 33 seconds, about 34 seconds, about 35 second, about 36 seconds, about 37 seconds, about 38 seconds, about 39 second, about 40 seconds, about 41 second, about 42 seconds, about 43 seconds, about 44 seconds, about 45 second, about 46 seconds, about 47 seconds, about 48 seconds, about 49 second, about 50 seconds, about 51 second, about 52 seconds, about 53 seconds, about 54 seconds, about 55 second, about 56 seconds, about 57 seconds, about 58 seconds, about 59 second, or about 60 seconds, or any ranges between these values.

For example, in some embodiments, the bolus dose of meloxicam is administered to the patient over the course of about 5 to about 45 seconds. In other embodiments, the bolus dose of meloxicam is administered to the patient over the course of about 10 to about 40 seconds. In still other embodiments, the bolus dose of meloxicam is administered to the patient over the course of about 15 to about 35 seconds. In some embodiments, the bolus dose of meloxicam is administered to the patient over the course of about 10 to about 30 seconds. In certain embodiments, the bolus dose of meloxicam is administered to the patient over the course of about 15 to about 30 seconds. In one embodiment, the bolus dose of meloxicam is administered to the patient over about 15 seconds.

Notably, the infusion rates of the present disclosure are significantly quicker than the FDA-approved infusion time of CALDOLOR® (an intravenous formulation of the NSAID ibuprofen), which requires at least 30 minutes. See CALDOLOR® Prescribing Information. Similarly, the infusion rates of the present disclosure are also significantly faster than infusion rates for OFIRMEV® (an intravenous formulation of acetaminophen), which requires a 15 minute infusion rate. See OFIRMEV® Prescribing Information. Whereas intravenous formulations of ibuprofen and acetaminophen cause injection site pain when administered at a rate that is faster than 15 minutes and 30 minutes, respectively, the present formulations were surprisingly discovered not to cause such injection site pain when administered in a bolus dose.

Further, the inventors discovered that injection of meloxicam in the bolus dose within seconds, according to the methods disclosed herein, achieves fast onset of analgesics which is critical for management of acute pain, such as post-surgical pain. For example, in one embodiment, the bolus dose of meloxicam administered intravenously to a patient can provide pain relief within about 10 minutes. This rapid onset of pain relief provided by the methods of the present disclosure represents a substantial improvement from available intravenous NSAIDs, such as ketorolac which can take up to 30 minutes for the onset of pain relief. See Ketorolac Tromethamine Injection Prescribing Information.

Moreover, unlike the previously reported NSAID injections which resulted in high injection site pain adverse effects (e.g., 16%-24% reported), the inventors found that the bolus injection methods for administration of meloxicam disclosed herein is safe and efficacious, as only 2% of patients receiving a bolus dose of intravenous meloxicam reported injection site pain.

In one embodiment of the methods disclosed herein, the bolus dose of meloxicam is in the range of from about 15 mg to about 180 mg, inclusive of all values and subranges therebetween. That is, the bolus dose of meloxicam may be about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, or about 180 mg, or any ranges between these values.

In some embodiments, the bolus dose of meloxicam is in the range of from about 15 mg to about 100 mg. In other embodiments, the bolus dose of meloxicam is in the range of from about 15 mg to about 80 mg. In some embodiments, the bolus dose of meloxicam is in the range of from about 20 mg to about 70 mg. In some embodiments, the bolus dose of meloxicam is in the range of from about 30 mg to about 60 mg. In some embodiments, the bolus dose of meloxicam is about 30 mg. In another embodiment, the bolus dose of meloxicam is about 60 mg.

In some embodiments, the intravenous meloxicam is formulated at a concentration of from about 10 mg/mL to about 50 mg/mL, e.g., about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, and about 60 mg/mL, inclusive of all values and subranges therebetween. In particular embodiments, the intravenous meloxicam is formulated at a concentration of about 30 mg/mL.

In one embodiment, the bolus dose of meloxicam as disclosed herein is administered once a day, twice a day, three times a day, every other day, or at a frequency deemed appropriate by a physician. In one embodiment, the bolus dose of meloxicam is administered once a day intravenously. In some embodiments, meloxicam is administered about every 16-26 hours (e.g., about 16, about 17, about 18, about 19, about 20, about 21, about 22, about 23, about 24, about 25, or 26 hours, inclusive of all values and subranges therebetween) until the patient is no longer in need thereof. As used herein, a "patient is no longer in need thereof" when the pain has subsided or the patient is discharged from the hospital. In some embodiments, meloxicam is administered intravenously about once every 6 hours, about once every 8 hours, about once every 12 hours, about once every 18 hours, about once every 24 hours, about once every 36 hours, about once about every 48 hours or at a frequency deemed appropriate by a physician. In particular embodiments, meloxicam is administered about once every 18-24 hours.

In some embodiments, the methods comprise administering meloxicam to a subject at about 18 hours, at about 24 hours, at about 36 hours, at about 48 hours, at about 54 hours, at about 72 hours, at about 96 hours, at about 5 days, at about 6 days, and so forth subsequent to the first dose of meloxicam administered to the subject.

In one embodiment, the bolus dose of meloxicam as disclosed herein can be administered to a subject about every 16 hours to about every 26 hours (e.g., about every 18-24 hours) for 1 day, 2 days, 3 days, 4 days, 5 days, 6 days, 7 days, 8 days, 9 days, 10 days, 11 days, 12 days, 13 days, 14 days, or at a duration and frequency deemed appropriate by a physician.

In one embodiment, a single bolus dose as disclosed herein can provide a rapid treatment which lasts for about 12 hours to about 48 hours. In one embodiment, a single bolus dose as disclosed herein can provide a rapid treatment which lasts for about 24 hours. The ability for the presently disclosed meloxicam formulation to provide treatment lasting about 24 hours represents a significant improvement over previously approved NSAID IV treatments, such as CALDOLOR® which requires infusion every 6 hours. See CALDOLOR® Prescribing Information.

In any of the methods disclosed herein, meloxicam can be administered for treatment of pain or for pain management. In one embodiment, meloxicam can be administered for the treatment or management of acute pain. In one embodiment, meloxicam can be administered for the treatment or management of moderate to severe pain. In one embodiment, meloxicam can be administered for the treatment or management of mild to moderate pain. In one embodiment, meloxicam can be administered for the treatment or management of acute moderate to severe pain. In one embodiment, meloxicam can be administered for the treatment or management of acute mild to moderate pain. In one embodiment, the pain management is for a human patient. In one embodiment, the human patient is an adult (e.g., aged 17 or older).

In one embodiment of the method as disclosed herein, the pain treated is post-surgical pain. Post-surgical pain may include two clinically important aspects, namely resting pain, or pain that occurs when the patient is not moving, and mechanical pain which is exacerbated by movement (coughing/sneezing, getting out of bed, physiotherapy, etc.). In some embodiments, resting pain is treated, in some embodiments, mechanically-induced pain (including pain resulting from movement) is treated, and in some embodiments, thermally-induced pain is treated. In some embodiments, allodynia (i.e., increased response (i.e., increased noxious sensation) to a normally non-noxious stimulus) is treated. In some embodiments, hyperalgesia (i.e., increased response to a normally noxious or unpleasant stimulus) is treated. In some embodiments, allodynia and/or hyperalgesia is thermal or mechanical (tactile) in nature, or resting pain. In some embodiments, the pain is associated with site of incision, wound or trauma, and/or proximal, at or near the site of incision, wound, and/or trauma. In some embodiments, the pain is nociceptive pain, including superficial somatic pain, deep somatic pain and visceral pain; in some embodiments, the pain is neuropathic pain such as central neuropathic pain and peripheral neuropathic pain.

In some embodiments, the surgical procedure is performed on hard and/or soft tissue. In some embodiments, the surgical procedure is performed on soft tissue. In some embodiments, the soft tissue surgery may include, but is not limited to, reproductive surgery, abdominal surgery, thoracic surgery, upper airway surgery, head and neck surgery, neurosurgery, surgical oncology and wound care and reconstruction. In some embodiments, soft tissues include, but are not limited to, tendons, ligaments, fascia, skin, fibrous tissues, fat, and synovial membranes (which are connective tissue), and muscles, nerves and blood vessels (which are not connective tissue). In other embodiments, the surgical procedure is performed on hard tissue. Hard or calcified tissues include tissues which are mineralized and have a firm intercellular matric. Non limiting examples of hard tissues are bone, tooth enamel, dentin, and cementum.

In some aspects, the surgery is open surgery, which refers to a procedure involving cutting of skin and tissues so that a surgeon has a full view of the structures or organs involved. Non-limiting examples of open surgery include removal of organs, such as gall bladder or kidneys, organ transplant, removal of a brain tumor, removal of a damaged kidney or open-heart surgery.

In some aspects, the surgery is a minimally invasive surgery, which refers to a procedure that typically does not involve generating a large incision. Non-limiting examples of minimally invasive surgery include laparoscopy, endoscopy, arthroscopy, bronchoscopy, cystoscopy, gastroscopy, hysteroscopy, laryngoscopy and sigmoidoscopy. In some embodiments, the surgical procedure is a laparoscopic surgical procedure. Typically, laparoscopy is a surgical procedure involving generating small incisions (cuts) in the wall of the abdomen and inserting a laparoscope (a thin, lighted tube) into one of the incisions. In some embodiments, during laparoscopy, other instruments may be inserted through the same or other incisions to perform procedures such as removing organs or taking tissue samples to be checked under a microscope for signs of disease. Non-limiting examples of laparoscopic procedures are gynecological surgery, lymphadenectomy, kidney surgery, radical prostatectomy, livery surgery, gallbladder removal (cholecystectomy), appendectomy, hernia repair, removal of part of the colon (colectomy) or small intestine, surgery for acid-reflux disease (fundoplication), removal of adrenal glands, and removal of the spleen. In some aspects, the surgery may be microsurgery, which typically is used for delicate work on very small body structures relying on special equipment and microscopes to magnify the area to be operated on and using tiny surgical instruments. Non-limiting examples of microsurgeries are vasectomy reversal or re-attaching a severed finger. In some embodiments, the surgery is robotic-assisted surgery, in which a surgeon maneuvers robotic arms during the procedure allowing for more precise movements. Non-limiting examples of robotic surgery include surgeries on the head and neck, gynecologic and urologic surgeries like hysterectomies and prostate cancer treatments.

In some embodiments, the surgery is colorectal surgery, while in other embodiments, the surgery is orthopedic surgery. In some embodiments, the surgery is joint replacement surgery. In some embodiments, the surgery is unilateral total knee arthroplasty.

In one embodiment of the method as disclosed herein, the dose of meloxicam is administered after the patient has undergone a surgical procedure. In one embodiment, the surgical procedure is an open surgical procedure. In another embodiment, the surgical procedure is a laparoscopic surgical procedure. In other embodiments, the surgical procedure was performed on hard tissue. In some embodiments, the surgical procedure was performed on soft tissue.

Formulations

In one embodiment, the bolus dose disclosed herein can comprise one or more pharmaceutically acceptable excipients or carriers known to one skilled in the art.

In one embodiment, a pharmaceutically acceptable excipient for the bolus dose for IV injection can include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, sodium deoxycholate (deoxycholic acid), starch tragacanth, sucrose and xanthan gum.

In one embodiment, the bolus dose disclosed herein for injection can be formulated in liquid carriers such as, but not limited to, water, dextrose in water, glucose in water, vegetable oil, alcohol, polyethylene glycol, propylene glycol, or glycerin. In one embodiment, the bolus dose disclosed herein for injection is formulated in sterile water.

In one embodiment, the bolus dose of meloxicam is in a form of aqueous dispersion.

In one embodiment of the method as disclosed herein, the bolus dose of meloxicam is present in a volume of from about 0.5 mL to about 4 mL, inclusive of all values and subranges therebetween. That is, the bolus dose of meloxicam is present in a volume of about 0.5 mL, about 0.6 mL, about 0.7 mL, about 0.8 mL, about 0.9 mL, about 1.0 mL, about 1.1 mL, about 1.2 mL, about 1.3 mL, about 1.4 mL, about 1.5 mL, about 1.6 mL, about 1.7 mL, about 1.8 mL, about 1.9 mL, about 2.0 mL, about 2.1 mL, about 2.2 mL, about 2.3 mL, about 2.4 mL, about 2.5 mL, about 2.6 mL, about 2.7 mL, about 2.8 mL, about 2.9 mL, about 3.0 mL, about 3.1 mL, about 3.2 mL, about 3.3 mL, about 3.4 mL, about 3.5 mL, about 3.6 mL, about 3.7 mL, about 3.8 mL, about 3.9 mL, or about 4.0 mL, or any ranges between these values. In another embodiment, the dose of meloxicam is present in a volume of about 1 mL.

In one embodiment of the method as disclosed herein, the dose of meloxicam is present at a concentration of about 15 mg/mL to about 30 mg/mL.

In one embodiment of the method as disclosed herein, the dose of meloxicam is present at a concentration of about 30 mg/mL. That is, the bolus dose of meloxicam can be present at a concentration between 28.5 mg/mL and 31.5 mg/mL or any subranges between the two values. In some embodiments, the dose of meloxicam can be present at a concentration of about 10 mg/mL to about 40 mg/mL, such as, for example, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, and about 40 mg/mL inclusive of all values and subranges therebetween.

In one embodiment, the bolus dose of meloxicam is present at a concentration of about 30 mg/mL as a single use vial.

As previously noted, meloxicam has poor water solubility, which is one of the main reasons oral administration is not suitable for treatment of acute pain. Further, due to meloxicam's poor water solubility, it is challenging to provide an injectable formulation that is sufficiently concentrated so that the formulation can be injected to patients in seconds in order to achieve rapid onset of pain relief without causing injection site pain. However, the inventors were able to increase the meloxicam concentration to 30 mg/mL. This is a 20% increase in the concentration of meloxicam as compared to an otherwise similar formulation in which meloxicam is not prepared as nanocrystals, which is substantial considering meloxicam is poorly water soluble. The concentration of meloxicam as disclosed herein is critical to providing a bolus dose and achieving rapid onset of pain relief without causing injection site pain. At concentrations of meloxicam which are higher than those disclosed herein, the drugs can crystallize out of solution, which will interfere with the injectability and/or syringeability of the formulation. At concentrations of meloxicam which are lower than those disclosed herein, the larger volumes of carrier preclude administration within the time ranges specified herein, and thus cannot achieve rapid onset of pain relief.

In one embodiment, the bolus dose of meloxicam as disclosed herein is used without dilution. In one embodiment, the 30 mg/mL bolus dose of meloxicam is used without dilution. In one embodiment, the 30 mg/mL bolus dose of meloxicam is not added to an IV solution or an IV fluid bag. That is, the 30 mg/mL bolus dose of meloxicam as disclosed herein is administered to a patient in need thereof as 30 mg/mL.

Pharmacokinetics

In one embodiment, 1 mL of a 30 mg/mL bolus dose provides an average maximum blood plasma concentration ($C_{max}$) within about 80% to about 125% of the range of from about 4000 ng/mL to about 11000 ng/mL in a patient after intravenous administration of 30 mg of meloxicam, inclusive of all values and subranges therebetween. That is, a single 30 mg/mL bolus dose can provide plasma $C_{max}$ of about 3000 ng/mL, about 3100 ng/mL, about 3200 ng/mL, about 3300 ng/mL, about 3400 ng/mL, about 3500 ng/mL, about 3600 ng/mL, about 3700 ng/mL, about 3800 ng/mL, about 3900 ng/mL, about 4000 ng/mL, about 4100 ng/mL, about 4200 ng/mL, about 4300 ng/mL, about 4400 ng/mL, about 4500 ng/mL, about 4600 ng/mL, about 4700 ng/mL, about 4800 ng/mL, about 4900 ng/mL, about 5000 ng/mL, about 5100 ng/mL, about 5200 ng/mL, about 5300 ng/mL, about 5400 ng/mL, about 5500 ng/mL, about 5600 ng/mL, about 5700 ng/mL, about 5800 ng/mL, about 5900 ng/mL, about 6000 ng/mL, about 6100 ng/mL, about 6200 ng/mL, about 6300 ng/mL, about 6400 ng/mL, about 6500 ng/mL, about 6600 ng/mL, about 6700 ng/mL, about 6800 ng/mL, about 6900 ng/mL, about 7000 ng/mL, about 7100 ng/mL, about 7200 ng/mL, about 7300 ng/mL, about 7400 ng/mL, about 7500 ng/mL, about 7600 ng/mL, about 7700 ng/mL, about 7800 ng/mL, about 7900 ng/mL, about 8000 ng/mL, about 8100 ng/mL, about 8200 ng/mL, about 8300 ng/mL, about 8400 ng/mL, about 8500 ng/mL, about 8600 ng/mL, about 8700 ng/mL, about 8800 ng/mL, about 8900 ng/mL, about 9000 ng/mL, about 9100 ng/mL, about 9200 ng/mL, about 9300 ng/mL, about 9400 ng/mL, about 9500 ng/mL, about 9600 ng/mL, about 9700 ng/mL, about 9800 ng/mL, about 9900 ng/mL, about 10000 ng/mL, about 10100 ng/mL, about 10200 ng/mL, about 10300 ng/mL, about 10400 ng/mL, about 10500 ng/mL, about 10600 ng/mL, about 10700 ng/mL, about 10800 ng/mL, about 10900 ng/mL, about 11000 ng/mL, about 11100 ng/mL, about 11200 ng/mL, about 11300 ng/mL, about 11400 ng/mL, about 11500 ng/mL, about 11600 ng/mL, about 11700 ng/mL, about 11800 ng/mL, about 11900 ng/mL, about 12000 ng/mL, about 12100 ng/mL, about 12200 ng/mL, about 12300 ng/mL, about 12400 ng/mL, about 12500 ng/mL, about 12600 ng/mL, about 12700 ng/mL, about 12800 ng/mL, about 12900 ng/mL, about 13000 ng/mL, about 13100 ng/mL, about 13200 ng/mL, about 13300 ng/mL, about 13400 ng/mL, and about 13500 ng/mL, or any values or ranges between above values, in a patient.

In one embodiment, 1 mL of a 30 mg/mL bolus dose provides an average plasma $C_{max}$ within the range of from about 80% to about 125% of 5642.9±1009.0 ng/mL in a patient after intravenous administration of intravenous meloxicam, inclusive of all values and subranges therebetween. In one embodiment, 1 mL of a 30 mg/mL bolus dose provides an average plasma $C_{max}$ within the range of from about 3707.1 ng/mL to about 8314.9 ng/mL in a patient after intravenous administration of intravenous meloxicam, inclusive of all values and subranges therebetween. In one embodiment, 1 mL of a 30 mg/mL bolus dose provides an average plasma $C_{max}$ within about 80% to about 125% of the range of from about 4000 ng/mL to about 7000 ng/mL in a patient after intravenous administration of 30 mg of meloxicam, inclusive of all values and subranges therebetween. In one embodiment, a single 30 mg/mL bolus dose provides an average plasma $C_{max}$ within about 80% to about 125% the range of from about 4600 ng/mL to about 6700 ng/mL in a patient after intravenous administration of intravenous meloxicam, inclusive of all values and subranges therebetween. In one embodiment, a single 30 mg/mL bolus dose provides an average plasma $C_{max}$ within about 80% to about 125% of the range of from about 5000 ng/mL to about 6000 ng/mL in a patient after intravenous administration of 30 mg of meloxicam, inclusive of all values and subranges therebetween.

In one embodiment, 1 mL of a 30 mg/mL bolus dose provides plasma $C_{max}$ within the range of from about 80% to about 125% of 7972.5±2579.0 ng/mL in a patient after intravenous administration of 30 mg of meloxicam, inclusive of all values and subranges therebetween. In one embodiment, 1 mL of a 30 mg/mL bolus dose provides plasma $C_{max}$ within the range of from about 4,312.1 ng/mL to about 13,190.5 ng/mL in a patient after intravenous administration of 30 mg of meloxicam, inclusive of all values and subranges therebetween. In one embodiment, 1 mL of a 30 mg/mL bolus dose provides an average plasma $C_{max}$ within the range of from about 80% to about 125% of about 5000 ng/mL to about 11000 ng/mL in a patient after intravenous administration of 30 mg of meloxicam, inclusive of all values and subranges therebetween. In one embodiment, 1 mL of a 30 mg/mL bolus dose provides an average plasma $C_{max}$ within about 80% to about 125% of the range of from about 5500 ng/mL to about 10500 ng/mL in a patient after intravenous administration of 30 mg of meloxicam, inclusive of all values and subranges therebetween. In one embodiment, 1 mL of a 30 mg/mL bolus dose provides an average plasma $C_{max}$ within the range of from about 80% to about 125% of about 7000 ng/mL to about 9000 ng/mL in a patient in a patient after intravenous administration of intravenous meloxicam, inclusive of all value sand subranges therebetween.

In one embodiment, a repeat dose (e.g., administered once daily) of a 1 mL of a 30 mg/mL bolus dose provides plasma $C_{max}$ within the range of from about 80% to about 125% of about 10632.5±4729.8 ng/mL in a patient after intravenous administration of 30 mg of meloxicam, inclusive of all values and subranges therebetween. In one embodiment, a repeat dose of a 30 mg/mL bolus dose provides plasma $C_{max}$ within the range of from about 4,722.2 ng/mL to about 19,202.9 ng/mL in a patient after intravenous administration of 30 mg of meloxicam, inclusive of all values and subranges therebetween. That is, a repeat dose of 1 mL of a 30 mg/mL bolus dose can provide plasma $C_{max}$ of about 4500 ng/mL, about 4600 ng/mL, about 4700 ng/mL, about 4800 ng/mL, about 4900 ng/mL, about 5000 ng/mL, about 5100 ng/mL, about 5200 ng/mL, about 5300 ng/mL, about 5400 ng/mL, about 5500 ng/mL, about 5600 ng/mL, about 5700 ng/mL, about 5800 ng/mL, about 5900 ng/mL, about 6000 ng/mL, about 6100 ng/mL, about 6200 ng/mL, about 6300 ng/mL, about 6400 ng/mL, about 6500 ng/mL, about 6600 ng/mL, about 6700 ng/mL, about 6800 ng/mL, about 6900 ng/mL, about 7000 ng/mL, about 7100 ng/mL, about 7200 ng/mL, about 7300 ng/mL, about 7400 ng/mL, about 7500 ng/mL, about 7600 ng/mL, about 7700 ng/mL, about 7800 ng/mL, about 7900 ng/mL, about 8000 ng/mL, about 8100 ng/mL, about 8200 ng/mL, about 8300 ng/mL, about 8400 ng/mL, about 8500 ng/mL, about 8600 ng/mL, about 8700 ng/mL, about 8800 ng/mL, about 8900 ng/mL, about 9000 ng/mL, about 9100 ng/mL, about 9200 ng/mL, about 9300 ng/mL, about 9400 ng/mL, about 9500 ng/mL, about 9600 ng/mL, about 9700 ng/mL, about 9800 ng/mL, about 9900 ng/mL, about 10000 ng/mL, about 10100 ng/mL, about 10200 ng/mL, about 10300 ng/mL, about 10400 ng/mL, about 10500 ng/mL, about 10600 ng/mL, about 10700 ng/mL, about 10800 ng/mL, about 10900 ng/mL, about 11000 ng/mL, about 11100 ng/mL, about 11200 ng/mL, about 11300 ng/mL, about 11400 ng/mL, about 11500 ng/mL, about 11600 ng/mL, about 11700 ng/mL, about 11800 ng/mL, about 11900 ng/mL, about 12000 ng/mL, about 12100 ng/mL, about 12200 ng/mL, about 12300 ng/mL, about 12400 ng/mL, about 12500 ng/mL, about 12600 ng/mL, about 12700 ng/mL, about 12800 ng/mL, about 12900 ng/mL, about 13000 ng/mL, about 13100 ng/mL, about 13200 ng/mL, about 13300 ng/mL, about 13400 ng/mL, about 13500 ng/mL, about 13600 ng/mL, about 13700 ng/mL, about 13800 ng/mL, about 13900 ng/mL, about 14000 ng/mL, about 14100 ng/mL, about 14200 ng/mL, about 14300 ng/mL, about 14400 ng/mL, about 14500 ng/mL, about 14600 ng/mL, about 14700 ng/mL, about 14800 ng/mL, about 14900 ng/mL, about 15000 ng/mL, about 15100 ng/mL, about 15200 ng/mL, about 15300 ng/mL, about 15400 ng/mL, about 15500 ng/mL, about 15600 ng/mL, about 15700 ng/mL, about 15800 ng/mL, about 15900 ng/mL, about 16000 ng/mL, about 16100 ng/mL, about 16200 ng/mL, about 16300 ng/mL, about 16400 ng/mL, about 16500 ng/mL, about 16600 ng/mL, about 16700 ng/mL, about 16800 ng/mL, about 16900 ng/mL, about 17000 ng/mL, about 17100 ng/mL, about 17200 ng/mL, about 17300 ng/mL, about 17400 ng/mL, about 17500 ng/mL, about 17600 ng/mL, about 17700 ng/mL, about 17800 ng/mL, about 17900 ng/mL, about 18000 ng/mL, about 18100 ng/mL, about 18200 ng/mL, about 18300 ng/mL, about 18400 ng/mL, about 18500 ng/mL, about 18600 ng/mL, about 18700 ng/mL, about 18800 ng/mL, about 18900 ng/mL, about 19000 ng/mL, about 19100 ng/mL, about 19200 ng/mL, about 19300 ng/mL, about 19400 ng/mL, about 19500 ng/mL, about 19600 ng/mL, about 19700 ng/mL, about 19800 ng/mL, about 19900 ng/mL, or about 12000 ng/mL, or any values or ranges between above values, in a patient.

In one embodiment, a repeat dose (e.g., once daily) of 1 mL of a 30 mg/mL bolus dose provides plasma $C_{max}$ within about 80% to about 125% of the range of from about 5000 ng/mL to about 20000 ng/mL in a patient after intravenous administration of 30 mg of meloxicam, inclusive of all values and subranges therebetween. In one embodiment, a repeat dose of 1 mL of a 30 mg/mL bolus dose provides an average plasma $C_{max}$ within about 80% to about 125% of the range of from of about 7000 ng/mL to about 18000 ng/mL in a patient after intravenous administration of 30 mg of meloxicam, inclusive of all values and subranges therebetween. In one embodiment, a repeat dose of 1 mL of a 30 mg/mL bolus dose provides an average plasma $C_{max}$ within the range of from about 80% to about 125% of about 8000 ng/mL to about 13000 ng/mL in a patient after intravenous administration of 30 mg of meloxicam, inclusive of all values and subranges therebetween.

In one embodiment, 1 mL of a 30 mg/mL bolus dose provides an average plasma $AUC_{inf}$ within about 80% to about 125% of the range of from about 55,000 ng*hr/mL to about 190,000 ng*hr/mL in a patient after intravenous administration of 30 mg of meloxicam, inclusive of all values and subranges therebetween. That is, 1 mL of a 30 mg/mL bolus dose can provide an average plasma $AUC_{inf}$ of about 40,000 ng*hr/mL, about 45,000 ng*hr/mL, about 50,000 ng*hr/mL, about 55,000 ng*hr/mL, about 60,000 ng*hr/mL, about 65,000 ng*hr/mL, about 70,000 ng*hr/mL, about 75,000 ng*hr/mL, about 80,000 ng*hr/mL, about 85,000 ng*hr/mL, about 90,000 ng*hr/mL, about 95,000 ng*hr/mL, about 100,000 ng*hr/mL, about 105,000 ng*hr/mL, about 110,000 ng*hr/mL, about 115,000 ng*hr/mL, about 120,000 ng*hr/mL, about 125,000 ng*hr/mL, about 130,000 ng*hr/mL, about 135,000 ng*hr/mL, about 140,000 ng*hr/mL, about 145,000 ng*hr/mL, about 150,000 ng*hr/mL, about 155,000 ng*hr/mL, about 160,000 ng*hr/mL, about 165,000 ng*hr/mL, about 170,000 ng*hr/mL, about 175,000 ng*hr/mL, about 180,000 ng*hr/mL, about 185,000 ng*hr/mL, about 190,000 ng*hr/mL, about 195,000 ng*hr/mL, about 200,000 ng*hr/mL, about 205,000 ng*hr/mL, about 210,000 ng*hr/mL, about 215,000 ng*hr/mL, about 220,000 ng*hr/mL, about 225,000 ng*hr/mL, about 230,000 ng*hr/mL about 235,000 ng*hr/mL, and about 240,000 ng*hr/mL, or any values or ranges between above values, in a patient.

In one embodiment, 1 mL of a 30 mg/mL bolus dose provides an average plasma $AUC_{inf}$ within the range of from about 80% to about 125% of about 107508.7±34443.0 ng*hr/mL in a patient after intravenous administration of 30 mg of meloxicam, inclusive of all values and subranges therebetween. In one embodiment, 1 mL of a 30 mg/mL bolus dose provides an average plasma $AUC_{inf}$ within the range of from about 58,452.6 ng*hr/mL to about 177,440.0 ng*hr/mL in a patient after intravenous administration of 30 mg of meloxicam, inclusive of all values and subranges therebetween. In one embodiment, 1 mL of a 30 mg/mL bolus dose provides an average plasma $AUC_{inf}$ within the range of from about 80% to about 125% of about 121437.6±64505.6 ng*hr/mL in a patient after intravenous administration of 30 mg of meloxicam, inclusive of all values and subranges therebetween. In one embodiment, 1 mL of a 30 mg/mL bolus dose provides an average plasma $AUC_{inf}$ within the range of from about 45,545.6 ng*hr/mL to about 232,429.0 ng*hr/mL in a patient after intravenous administration of 30 mg of meloxicam, inclusive of all values and subranges therebetween. In one embodiment, a 1 mL of a 30 mg/mL bolus dose provides an average plasma $AUC_{inf}$ of about 70,000 ng*hr/mL to about 190,000 ng*hr/mL in a patient after intravenous administration of 30 mg of meloxicam, inclusive of all values and subranges therebetween. In one embodiment, 1 mL of a 30 mg/mL bolus dose provides an average plasma $AUC_{inf}$ within the range of from about 80% to about 125% of about 70,000 ng*hr/mL to about 140,000 ng*hr/mL in a patient after intravenous administration of 30 mg of meloxicam, inclusive of all values and subranges therebetween. In one embodiment, 1 mL of a 30 mg/mL bolus dose provides an average plasma $AUC_{inf}$ within about 80% to about 125% of the range of from about 75,000 ng*hr/mL to about 130,000 ng*hr/mL in a patient after intravenous administration of 30 mg of meloxicam, inclusive of all values and subranges therebetween. In one embodiment, 1 mL of a 30 mg/mL bolus dose provides an average plasma $AUC_{inf}$ within about 80% to about 125% of the range of from about 85,000 ng*hr/mL to about 120,000 ng*hr/mL in a patient after intravenous administration of 30 mg of meloxicam, inclusive of all values and subranges therebetween. In one embodiment, 1 mL of a 30 mg/mL bolus dose provides an average plasma $AUC_{inf}$ within about 80% to about 125% of the range of from about 55,000 ng*hr/mL to about 190,000 ng*hr/mL in a patient after intravenous administration of 30 mg of meloxicam, inclusive of all values and subranges therebetween. In one embodiment, 1 mL of a 30 mg/mL bolus dose provides an average plasma $AUC_{inf}$ within about 80% to about 125% of the range of from about 80,000 ng*hr/mL to about 160,000 ng*hr/mL in a patient after intravenous administration of 30 mg of meloxicam, inclusive of all values and subranges therebetween. In one embodiment, 1 mL of a 30 mg/mL bolus dose provides an average plasma $AUC_{inf}$ within about 80% to about 125% of the range of from about 100,000 ng*hr/mL to about 140,000 ng*hr/mL in a patient after intravenous administration of 30 mg of meloxicam, inclusive of all values and subranges therebetween.

In one embodiment, a repeat dose (e.g., once daily) of 1 mL of a 30 mg/mL bolus dose provides plasma $AUC_{inf}$ within the range of from about 80% to about 125% of about 297,771.6±241,604.01 ng*hr/mL in a patient after intravenous administration of 30 mg of meloxicam, inclusive of all values and subranges therebetween. In one embodiment, a repeat dose of 1 mL of a 30 mg/mL bolus dose provides plasma $AUC_{inf}$ within the range of from about 44,934.1 ng*hr/mL to about 674,219.5 ng*hr/mL in a patient after intravenous administration of 30 mg of meloxicam, inclusive of all values and subranges therebetween. In one embodiment, a repeat dose of 1 mL of a 30 mg/mL bolus dose provides an average plasma $AUC_{inf}$ within about 80% to about 125% of the range of from about 55,000 ng*hr/mL to about 540,000 ng*hr/mL in a patient after intravenous administration of 30 mg of meloxicam, inclusive of all values and subranges therebetween. In one embodiment, a repeat dose of 1 mL of a 30 mg/mL bolus dose provides an average plasma $AUC_{inf}$ within about 80% to about 125% of the range of from about 80,000 ng*hr/mL to about 500,000 ng*hr/mL in a patient after intravenous administration of 30 mg of meloxicam, inclusive of all values and subranges therebetween. In one embodiment, a repeat dose of 1 mL of a 30 mg/mL bolus dose provides an average plasma $AUC_{inf}$ within about 80% to about 125% of the range of from about 100,000 ng*hr/mL to about 450,000 ng*hr/mL in a patient after intravenous administration of 30 mg of meloxicam, inclusive of all values and subranges therebetween. In one embodiment, a repeat dose of 1 mL of a 30 mg/mL bolus dose provides an average plasma $AUC_{inf}$ within about 80% to about 125% of the range of from about 150,000 ng*hr/mL to about 400,000 ng*hr/mL in a patient after intravenous administration of 30 mg of meloxicam, inclusive of all values and subranges therebetween. In one embodiment, a repeat dose of 1 mL of a 30 mg/mL bolus dose provides an average plasma $AUC_{inf}$ within about 80% to about 125% of the range of from about 200,000 ng*hr/mL to about 350,000 ng*hr/mL in a patient after intravenous administration of 30 mg of meloxicam, inclusive of all values and subranges therebetween. In one embodiment, a repeat dose of 1 mL of a 30 mg/mL bolus dose provides an average plasma $AUC_{inf}$ within about 80% to about 125% of the range of from about 250,000 ng*hr/mL to about 325,000 ng*hr/mL in a patient after intravenous administration of 30 mg of meloxicam, inclusive of all values and subranges therebetween.

In one embodiment, steady state can be achieved upon repeat dose of a 30 mg bolus dose administered intravenously once daily for 7 days.

In one embodiment, 1 mL of a 30 mg/mL bolus IV dose provides an average plasma $T_{max}$ of about 0.05 h to about 0.20 h in a patient after intravenous administration of 30 mg of meloxicam, inclusive of all values and subranges therebetween. That is, a single 30 mg/mL bolus IV injection can provide an average plasma $T_{max}$ of about 0.05 h, about 0.06 h, about 0.07 h, about 0.08 h, about 0.09 h, about 0.10 h, about 0.11 h, about 0.12 h, about 0.13 h, about 0.14 h, about 0.15 h, about 0.16 h, about 0.17 h, about 0.18 h, about 0.19 h, or about 0.20 h, or any values or ranges between above values, in a patient.

In one embodiment, 1 mL of a 30 mg/mL bolus dose provides an average plasma $T_{max}$ of about 0.08 h to about 0.16 h in a patient after intravenous administration of 30 mg of meloxicam, inclusive of all values and subranges therebetween. In one embodiment, 1 mL of a 30 mg/mL bolus dose provides an average plasma $T_{max}$ of about 0.10 h to about 0.14 h in a patient after intravenous administration of 30 mg of meloxicam, inclusive of all values and subranges therebetween.

An orally administered meloxicam has a prolonged absorption, with a mean plasma $T_{max}$ of about 5-7 hours following administration. The methods as disclosed herein provides significantly faster $T_{max}$, e.g., about 0.08 h to about 0.16 h following administration, which is indicative of rapid onset and fast absorption.

In one embodiment, the method as disclosed herein can provide meloxicam peak analgesic effect within about 30 minutes to about 60 minutes. That is, the administration of 30 mg/mL bolus IV injection of meloxicam can provide peak analgesic effect in about 30 minutes, about 35 minutes, about 40 minutes, about 45 minutes, about 50 minutes, about 55 minutes, or about 60 minutes, or any values or ranges between above values. In one embodiment, the administration of 30 mg/mL bolus IV injection of meloxicam can provide peak analgesic effect in about 40 minutes.

Not only is the meloxicam administration as disclosed herein provide a fast onset of pain relief, it also reaches peak analgesic effect sooner than other known IV NSAIDs (Ketorolac can take 1 to 2 hours for maximum effect) and has a longer therapeutic window of at least about 24 hours (Ketorolac's duration of analgesic effect is 4 to 6 hours). See Ketorolac Tromethamine Injection Prescribing Information.

In one embodiment, 1 mL of a 30 mg/mL bolus dose of meloxicam provides an average plasma concentration in the range of from about 80% to about 125% of 4160±1020 ng/mL of meloxicam in a patient at about 30 minutes after intravenous administration, inclusive of all values and subranges therebetween. In one embodiment, 1 mL of a 30 mg/mL bolus dose of meloxicam provides an average plasma concentration in the range of from about 2512 ng/mL to about 6475 ng/mL of meloxicam in a patient at about 30 minutes after intravenous administration, inclusive of all values and subranges therebetween. In some embodiments, 1 mL of a 30 mg/mL bolus dose of meloxicam provides an average plasma concentration in the range of from about 3000 ng/mL to about 6000 ng/mL of meloxicam in a patient at about 30 minutes after intravenous administration, inclusive of all values and subranges therebetween. In other embodiments, 1 mL of a 30 mg/mL bolus dose of meloxicam provides an average plasma concentration in the range of from about 3500 ng/mL to about 5500 ng/mL of meloxicam in a patient at about 30 minutes after intravenous administration, inclusive of all values and subranges therebetween. In some embodiments, a single 30 mg/mL bolus dose of meloxicam provides an average plasma concentration in the range of from about 3500 ng/mL to about 5000 ng/mL of meloxicam in a patient at about 30 minutes after intravenous administration, inclusive of all values and subranges therebetween.

In one embodiment, 1 mL of a 30 mg/mL bolus dose of meloxicam provides an average plasma concentration in the range of from about 80% to about 125% of 3590±708 ng/mL of meloxicam in a patient at about 60 minutes after intravenous administration, inclusive of all values and subranges therebetween. In one embodiment, 1 mL of a 30 mg/mL bolus dose of meloxicam provides an average plasma concentration in the range of from about 2305 ng/mL to about 5373 ng/mL of meloxicam in a patient at about 60 minutes after intravenous administration, inclusive of all values and subranges therebetween. In some embodiments, 1 mL of a 30 mg/mL bolus dose of meloxicam provides an average plasma concentration in the range of from about 2500 ng/mL to about 5000 ng/mL of meloxicam in a patient at about 60 minutes after intravenous administration, inclusive of all values and subranges therebetween. In other embodiments, 1 mL of a 30 mg/mL bolus dose of meloxicam provides an average plasma concentration in the range of from about 2750 ng/mL to about 4500 ng/mL of meloxicam in a patient at about 60 minutes after intravenous administration, inclusive of all values and subranges therebetween. In some embodiments, a single 30 mg/mL bolus dose of meloxicam provides an average plasma concentration in the range of from about 3000 ng/mL to about 4000 ng/mL of meloxicam in a patient at about 60 minutes after intravenous administration, inclusive of all values and subranges therebetween.

In one embodiment, a single 30 mg/mL bolus dose of meloxicam provides an average plasma concentration in the range of from about 80% to about 125% of 2660±394 ng/mL of meloxicam in a patient at about 120 minutes after intravenous administration, inclusive of all values and subranges therebetween. In one embodiment, a single 30 mg/mL bolus dose of meloxicam provides an average plasma concentration in the range of from about 1812 ng/mL to about 3818 ng/mL of meloxicam in a patient at about 120 minutes after intravenous administration, inclusive of all values and subranges therebetween. In some embodiments, a single 30 mg/mL bolus dose of meloxicam provides an average plasma concentration in the range of from about 1900 ng/mL to about 3800 ng/mL of meloxicam in a patient at about 120 minutes after intravenous administration, inclusive of all values and subranges therebetween. In other embodiments, a single 30 mg/mL bolus dose of meloxicam provides an average plasma concentration in the range of from about 2100 ng/mL to about 3600 ng/mL of meloxicam in a patient at about 120 minutes after intravenous administration, inclusive of all values and subranges therebetween. In some embodiments, a single 30 mg/mL bolus dose of meloxicam provides an average plasma concentration in the range of from about 2200 ng/mL to about 3400 ng/mL of meloxicam in a patient at about 120 minutes after intravenous administration, inclusive of all values and subranges therebetween.

In one embodiment, a single 30 mg/mL bolus dose of meloxicam provides an average plasma concentration in the range of from about 80% to about 125% of 2190±262 ng/mL of meloxicam in a patient at about 4 hours after intravenous administration, inclusive of all values and subranges therebetween. In one embodiment, a single 30 mg/mL bolus dose of meloxicam provides an average plasma concentration in the range of from about 1542 ng/mL to about 3065 ng/mL of meloxicam in a patient at about 4 hours after intravenous administration, inclusive of all values and subranges therebetween. In some embodiments, a single 30 mg/mL bolus dose of meloxicam provides an average plasma concentration in the range of from about 1600 ng/mL to about 3000 ng/mL of meloxicam in a patient at about 4 hours after intravenous administration, inclusive of all values and subranges therebetween. In other embodiments, a single 30 mg/mL bolus dose of meloxicam provides an average plasma concentration in the range of from about 1800 ng/mL to about 2800 ng/mL of meloxicam in a patient at about 4 hours after intravenous administration, inclusive of all values and subranges therebetween. In some embodiments, a single 30 mg/mL bolus dose of meloxicam provides an average plasma concentration in the range of from about 1900 ng/mL to about 2600 ng/mL of meloxicam in a patient at about 4 hours after intravenous administration, inclusive of all values and subranges therebetween.

EXAMPLES

Example 1: Meloxicam 30 mg IV Injection Formulation

IV injection formulation is prepared as a ready-to-use formulation containing 30 mg NanoCrystal Colloidal Dispersion® meloxicam, povidone, sodium deoxycholate (deoxycholic acid), sucrose, and water for injection with a total volume of 1 mL in a ready-to-use vial.

Example 2: Treatment of Acute Moderate to Severe Pain with 30 mg/mL Meloxicam Bolus IV Injection Following Abdominoplasty This multicenter, randomized, double-blind, placebo-controlled trial evaluated the efficacy and safety of meloxicam in 219 subjects with moderate to severe pain following abdominoplasty. Subjects were enrolled and randomized to treatment (1:1 ratio) with meloxicam 30 mg (administered as 1 mL of 30 mg/mL) or placebo administered via IV push every 24 hours for up to three doses. Participation consisted of a screening visit, surgery and inpatient evaluation, and 2 follow-up visits, 7 and 28 days after last study dose.

Following abdominoplasty, subjects could be maintained using IV fentanyl until eligible to randomize to treatment. Study doses were administered as an IV infusion over approximately 15 seconds every 24 hours for a minimum of two doses, with an optional third dose prior to discharge.

Figure 1:
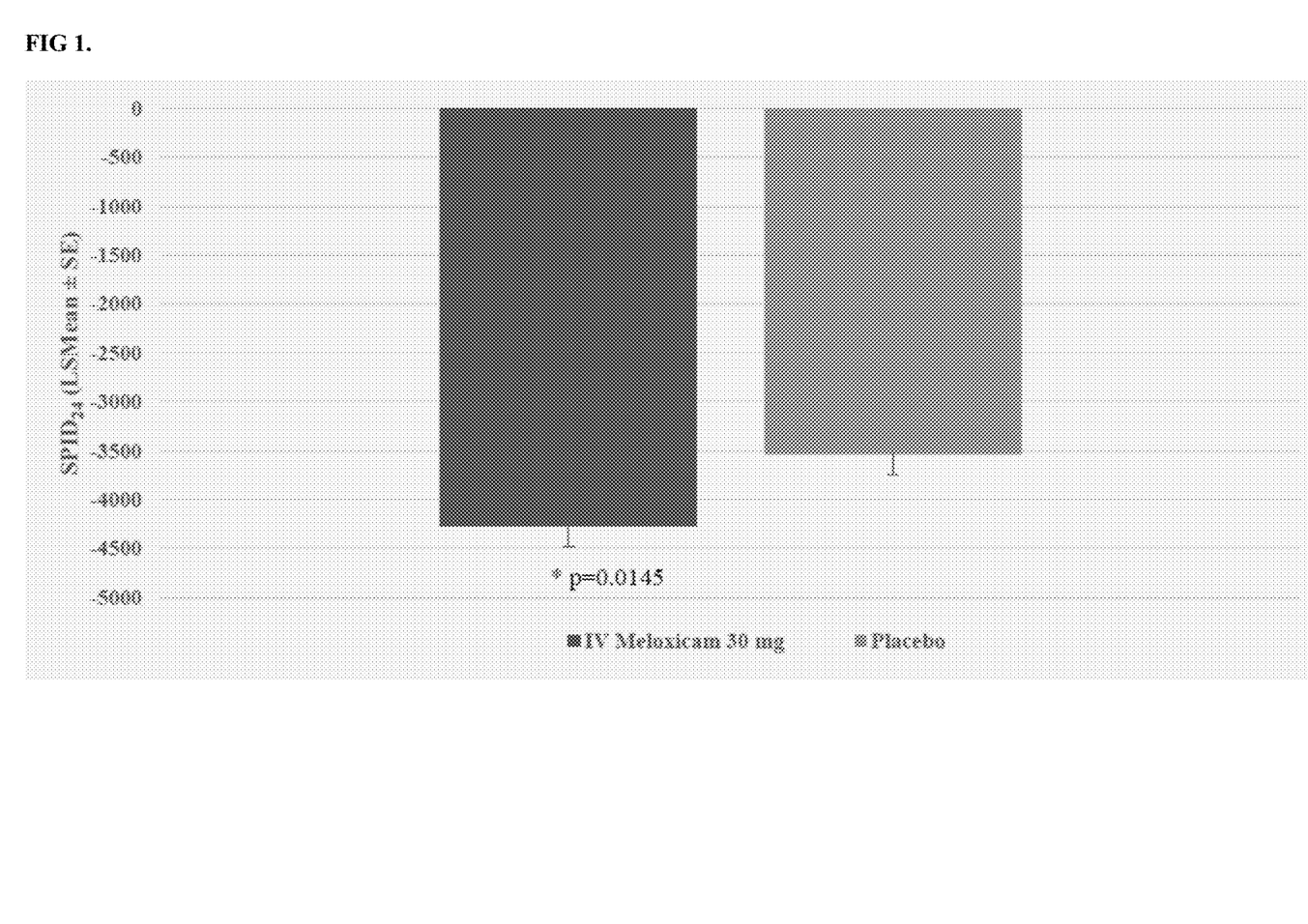
FIG. 1 shows the difference in the summed pain intensity difference over the first 24 hours ($SPID_{24}$) in subjects with moderate to severe pain following abdominoplasty surgery.

Baseline characteristics were similar between groups, with a mean pain intensity (numeric pain rating scale, 0-10) of 7.2 in the meloxicam group and 7.4 in the placebo group. In the primary efficacy assessment, meloxicam group demonstrated a statistically significant reduction in the summed pain intensity difference (SPID) through 24 hours following Dose 1 ($SPID_{24}$; p=0.0145) compared to the placebo group (FIG. 1). Sensitivity analyses of the $SPID_{24}$ each showed that the IV meloxicam 30 mg treated subjects had numerically greater total pain reduction (i.e., a smaller SPID value) compared with placebo treated subjects.

Statistically significant reductions in SPID were also observed through 12 hours ($SPID_{12}$; p=0.0434) and 48 hours post Dose 1 ($SPID_{48}$; p=0.0040) compared with placebo (Table 1). SPID assessed at other postdose intervals ($SPID_6$, $SPID_{12}$, $SPID_{48}$, and $SPID_{24-48}$) favored IV meloxicam at all intervals, and reached statistical significance at all but the $SPID_6$ interval (p<0.05). End of dose intervals ($SPID_{12-24}$, $SPID_{18-24}$, $SPID_{36-48}$, and $SPID_{42-48}$) numerically favored IV meloxicam 30 mg over placebo at each interval, and achieved statistical significance at all but the $SPID_{18-24}$ interval, suggesting that IV meloxicam 30 mg maintains meaningful analgesia throughout the 24 hours dosing interval.

TABLE 1

SPID (Leas-Squares Mean ± Standard Error)

| Parameter | IV Meloxicam 30 mg (N = 110) | Placebo (N = 109) | p-value |
|---|---|---|---|
| $SPID_6$ | −607.0 (52.45) | −510.9 (52.66) | 0.1841 |
| $SPID_{12}$ | −1763.8 (104.77) | −1471.1 (105.18) | 0.0434 |
| $SPID_{48}$ | −10600.0 (442.31) | −8829.2 (444.08) | 0.0040 |
| $SPID_{12-24}$ | −2498.3 (123.63) | −2064.7 (124.12) | 0.0115 |
| $SPID_{36-48}$ | −3276.2 (128.54) | −2827.6 (129.05) | 0.0119 |

Figure 2:
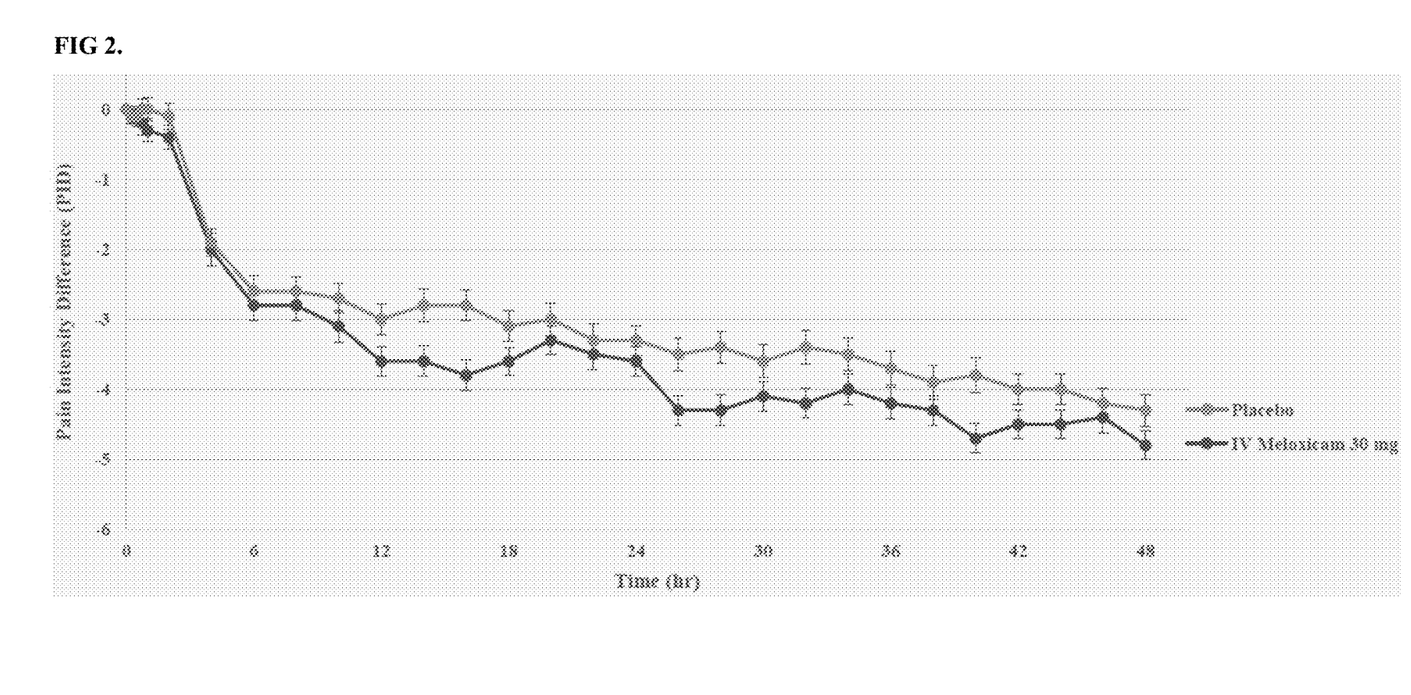
FIG. 2 shows pain intensity difference over time in subjects with moderate to severe pain following abdominoplasty surgery.

Pain intensity difference (PID) was calculated as the difference in pain intensity at each postdose time point compared with base line (FIG. 2). PID was lower in the IV meloxicam 30 mg group compared with placebo at all time points after 30 minutes postdose. PID values were equal prior to 30 minutes post dose.

The study achieved numerous other secondary endpoints, including statistically significant differences in time to perceptible pain relief (p=0.0050), number of subjects with ≥30% improvement in pain reduction at 24 hours (p=0.0178), number of times subjects required rescue analgesia in the first 24 hours (p=0.0275) and from 24 to 48 hours (p=0.0009), along with other pain endpoints.

Figure 3:
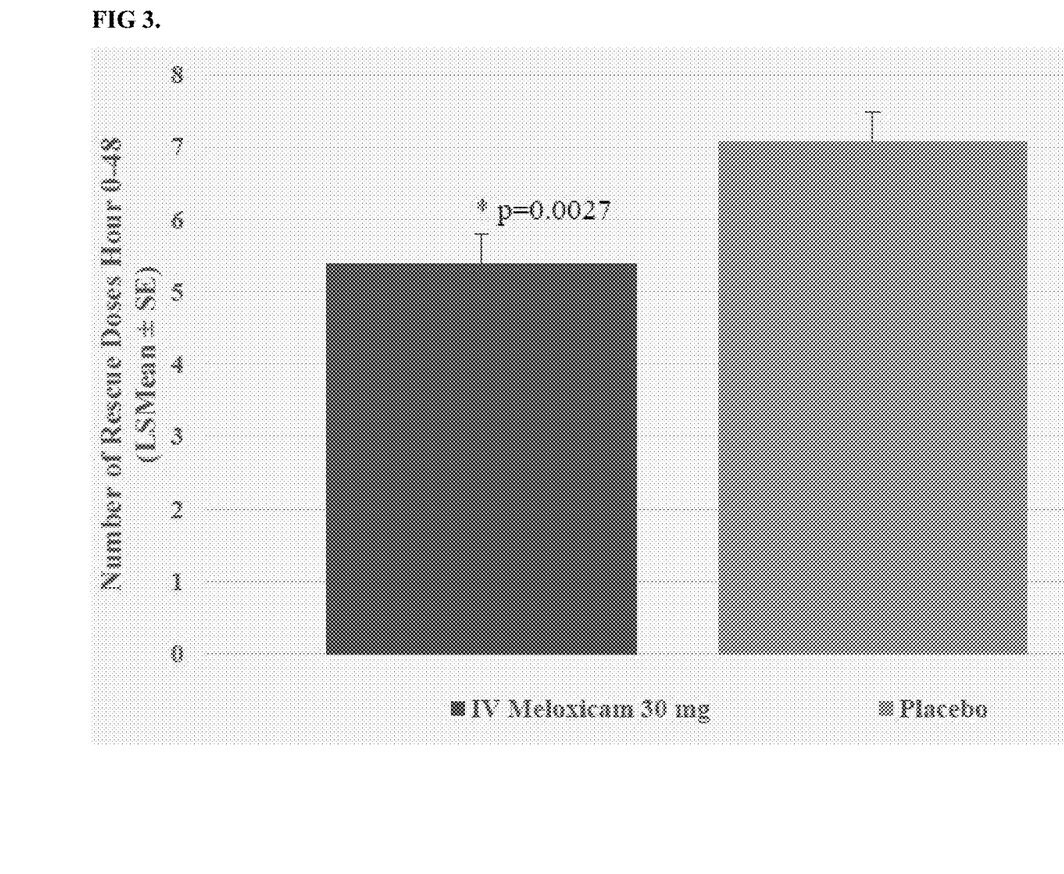
FIG. 3 shows number of rescue analgesia doses from hour 0-48 for subject with moderate to severe pain following abdominoplasty surgery.

Rescue analgesia (oxycodone 5 mg PO) was available to subjects with inadequately controlled pain during the treatment phase. The number of rescue doses utilized per subject was significantly lower in each assessed study interval (Hour 0-24, Hour 24-48, and Hour 0-48) in the IV meloxicam 30 mg group compared with placebo (p<0.05). The number of subjects utilizing rescue in each assessed study interval (Hour 0-24, Hour 24-48, and Hour 0-48) was numerically lower in the IV meloxicam 30 mg group compared with placebo (FIG. 3). No difference was observed in the time to first rescue use.

The safety results demonstrated that meloxicam was well tolerated with no difference in adverse event (AE) reporting between the groups. Two serious AEs (SAEs) related to bleeding were reported (one event in each treatment group), with two additional SAEs reported in the placebo group. The most common (≥2%) treatment-emergent AEs (TEAEs) in meloxicam treated subjects were nausea, headache, vomiting, and dizziness, which were observed at a lower incidence than in the placebo group. The majority of TEAEs were mild in intensity, with one subject discontinuing treatment due to an SAE of post-procedural bleeding (placebo). Investigator assessments of satisfaction with wound healing and various wound characteristics were comparable between meloxicam and placebo groups. There were no meaningful differences between treatment groups in vital signs, ECGs, or clinical laboratory assessments. Notably, only 2 subjects (1.8%; n=110) in meloxicam group reported of injection site pain.

The data from this study demonstrated that meloxicam provided significant pain relief in subjects with moderate to severe pain following abdominoplasty surgery, with a favorable safety and tolerability profile, as evidenced by $SPID_{24}$ results and the reduction in opioid rescue use. This study also demonstrated that once daily dosing with IV meloxcam maintained analgesia over the 24-hour dosing interval.

Example 3: Pharmacokinetics of 30 mg Meloxicam Bolus Dose

This study included 6 subjects (3 male, 3 female), ages 18 to 55 years with normal renal function (GFR≥90 mL/min/1.73 $m^2$).

Enrolled subjects returned to the study center on the day before dosing (Day −1). During the treatment visit (Day −1 to Day 3), subjects received a single IV dose 30 mg (administered at a concentration of 25 mg/mL) meloxicam over infusion time of 15-30 seconds. Whole blood samples were collected for pharmacokinetic (PK) analysis prior to dosing and 5, 10, 20, 30, and 45 minutes, and 1, 2, 4, 6, 12, 18, 24, 36, and 48 hours after dosing.

Subjects were asked to return to the study center daily for PK sampling at Hour 72 (Day 4), Hour 96 (Day 5), Hour 120 (Day 6), and Hour 144 (Day 7).

Pharmacokinetics

Meloxicam plasma concentrations and PK parameters observed for $T_{max}$ was 0.08 hours for all subjects, plasma $C_{max}$ geometric mean was 5580 ng/mL, and mean t½ was 17.5 h (Table 2). The plasma $AUC_{0-\infty}$ (area under the concentration-time curve from time 0 to infinity) geometric mean was 65100 hr·ng/mL (Table 2). The plasma $AUC_{0-t}$ (area under the concentration-time curve from time 0 to last time point with measurable concentration) results were similar to plasma $AUC_{0-\infty}$.

TABLE 2

Summary (Mean ± Standard Deviation (SD)) of PK Parameters

| Parameter | N | Mean ± SD |
|---|---|---|
| $C_{max}$, ng/mL | 6 | 5620 ± 713 |
| $T_{max}$, $h^a$ | 6 | 0.08 (0.08-0.08) |
| $AUC_{0-6}$, h · ng/mL | 6 | 16300 ± 2170 |
| $AUC_{0-12}$, h · ng/mL | 6 | 26400 ± 3920 |
| $AUC_{0-24}$, h · ng/mL | 6 | 41000 ± 8670 |
| $AUC_{0-t}$, h · ng/mL | 6 | 67900 ± 22500 |

TABLE 2-continued

Summary (Mean ± Standard Deviation (SD)) of PK Parameters

| Parameter | N | Mean ± SD |
|---|---|---|
| $AUC_{0-\infty}$, h · ng/mL | 6 | 68500 ± 22800 |
| t½, h | 6 | 17.5 ± 5.16 |

[a]Median (range).
$AUC_{0-6}$ = area under the concentration-time curve from time 0 to 6 hours after dosing
$AUC_{0-12}$ = area under the concentration-time curve from time 0 to 12 hours after dosing
$AUC_{0-24}$ = area under the concentration-time curve from time 0 to 24 hours after dosing
$AUC_{0-t}$ = area under the concentration-time curve from time 0 to last time point with measurable concentration
$AUC_{0-\infty}$ = area under the concentration-time curve from time 0 to infinity As demonstrated in Table 2, the 30 mg IV dose of meloxicam administered over 15- to 30-second infusion time has a rapid onset and fast absorption as demonstrated by $T_{max}$ of 0.08 h (4.8 minutes). The observed PK parameter, especially in the first several hours, is unique to IV bolus dose of meloxicam as oral meloxicam (e.g., Mobic®) requires about 5-7 hours to reach $T_{max}$ after administration. The mean plasma concentration of meloxicam at each time point is shown in Table 3.

TABLE 3

Summary (Mean ± SD) of Meloxicam Plasma Concentration (ng/mL)

| Time Point | (N = 6) |
|---|---|
| Pre-Dose | 0 ± 0.00 |
| 5 min | 5620 ± 713 |
| 10 min | 5030 ± 986 |
| 20 min | 4330 ± 864 |
| 30 min | 4160 ± 1020 |
| 45 min | 3720 ± 801 |
| 1 hour | 3590 ± 708 |
| 2 hours | 2660 ± 394 |
| 4 hours | 2190 ± 262 |
| 6 hours | 1880 ± 355 |
| 12 hours | 1490 ± 351 |
| 18 hours | 1230 ± 478 |
| 24 hours | 963 ± 339 |
| 36 hours | 578 ± 251 |
| 48 hours | 419 ± 246 |
| 72 hours | 200 ± 144 |
| 96 hours | 84.7 ± 68.1 |
| 120 hours | 33.1 ± 31.1 |
| 144 hours | 13.8 ± 15.2 |

Furthermore, a summary from an additional study including 7 healthy subjects receiving a single dose IV administration of 30 mg meloxicam (infusion time of 1 minute) is shown in Table 4.

TABLE 4

Summary of a Single-dose Pharmacokinetics of 30 mg Meloxicam Bolus Dose (n = 7)

| Parameter | Meloxicam 30 mg IV |
|---|---|
| $C_{max}$ (ng/mL) | 5642.9 ± 1009.0 |
| $T_{max}$ (h) | 0.12 ± 0.04 |
| $AUC_{inf}$ (ng * hr/mL) | 107508.7 ± 34443.0 |
| T½ (h) | 23.3 ± 9.36 |

Lastly, a summary from yet another study comparing PK parameters in healthy subjects following single and repeat doses (7 consecutive days of dosing, once a day) of 30 mg meloxicam intravenous dose is shown in Table 5.

TABLE 5

Summary of a Repeat-dose Pharmacokinetics of 30 mg Meloxicam Intravenous Dose (n = 8)

| Parameter | Meloxicam 30 mg IV Single Dose | Meloxicam 30 mg IV Repeat Dose |
|---|---|---|
| $C_{max}$ (ng/mL) | 7972.5 ± 2579.9 | 10632.5 ± 4729.8 |
| $AUC_{inf}$ (ng · hr/mL) | 121437.6 ± 64505.6 | 297771.6 ± 241604.01 |
| T½ (h) | 23.6 ± 10.1 | 26.4 ± 10.1 |

The disclosures of all publications, patents, patent applications and published patent applications referred to herein by an identifying citation are hereby incorporated herein by reference in their entirety.

In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A method of treating moderate to severe pain in an adult human patient in need thereof with meloxicam, comprising administering intravenously once a day to the patient a first bolus dose of about 1 mL of a 30 mg/mL meloxicam nanocrystal aqueous dispersion; and further comprising administering intravenously a repeat bolus dose of about 1 mL of a 30 mg/mL meloxicam nanocrystal aqueous dispersion to the adult human patient about every 24 hours subsequent to the first dose; wherein the adult human patient has a reduction in summed pain intensity difference and a reduction in rescue analgesic use 48 hours after administration of the first bolus dose, and the repeat bolus dose; and wherein each of the bolus dose of about 1 mL of a 30 mg/mL meloxicam nanocrystal aqueous dispersion consists of:
   30 mg meloxicam nanocrystals;
   povidone;
   sodium deoxycholate;
   an excipient;
   and water.

2. The method of claim 1, wherein the pain is post-surgical pain.

3. The method of claim 1, wherein the meloxicam is administered after the adult human patient has undergone a surgical procedure.

4. The method of claim 3, wherein the surgical procedure is an open surgical procedure.

5. The method of claim 3, wherein the surgical procedure is a laparoscopic surgical procedure.

6. The method of claim 3, wherein the surgical procedure was performed on hard tissue.

7. The method of claim 3, wherein the surgical procedure was performed on soft tissue.

8. The method of claim 1, the summed pain intensity difference through 24 hours following the first bolus dose and the repeat bolus dose is about −4262.1.

9. The method of claim 1, the summed pain intensity difference through 48 hours following the first bolus dose is −10600.0 (±442.31).

10. The method of claim 1, wherein the excipient is selected from the group consisting of acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, propylene carbonate, propylene glycol alginate, sodium alginate, sodium starch glycolate, starch tragacanth, sucrose and xanthan gum.

11. The method of claim 1, wherein the excipient is sucrose.

12. The method of claim 1, wherein pain is treated in the adult human patient without administration of an opioid.

13. The method of claim 1, wherein the repeat bolus dose is administered for 48 hours.

\* \* \* \* \*